(12) United States Patent
Montgomery

(10) Patent No.: US 7,094,266 B2
(45) Date of Patent: Aug. 22, 2006

(54) MULTIPURPOSE, SELF-CONTAINED, PORTABLE AND ODOR-FREE WORKSTATION

(76) Inventor: Robert D. Montgomery, 1685 W. 12th St., Reno, NV (US) 89503

( * ) Notice: Subject to any disclaimer, the term of this patent is extended or adjusted under 35 U.S.C. 154(b) by 92 days.

(21) Appl. No.: 10/826,462

(22) Filed: Apr. 16, 2004

(65) Prior Publication Data

US 2005/0229555 A1    Oct. 20, 2005

(51) Int. Cl.
*B01D 50/00* (2006.01)
(52) U.S. Cl. .................. 55/385.1; 55/356; 55/385.2; 55/485; 55/380; 55/DIG. 18; 55/96; 96/415; 96/416; 454/187; 454/67; 128/207.14; 128/207.15; 604/332
(58) Field of Classification Search .................. 55/356, 55/385.1, 385.2, 485, 380, DIG. 18, 96; 454/67, 454/487; 96/415, 416; 128/207.14, 207.15; 604/332
See application file for complete search history.

(56) References Cited

U.S. PATENT DOCUMENTS 4,163,650 A * 8/1979 Watson et al. ................ 96/57
5,281,246 A * 1/1994 Ray et al. .................... 55/302
5,312,465 A * 5/1994 Riutta ......................... 55/320
6,066,195 A * 5/2000 Ko ............................... 96/416
6,203,590 B1 * 3/2001 Byrd et al. ................... 55/319
6,332,308 B1 * 12/2001 Miller ....................... 55/385.5
6,780,213 B1 * 8/2004 Chang et al. .............. 55/385.2
6,811,593 B1 * 11/2004 Hansson et al. .............. 95/273

* cited by examiner

Primary Examiner—Minh-Chau T. Pham

(57) ABSTRACT

A novel sanitary and odor free workstation having two spaced apart, transparent plate members that are operatively interconnected to a vacuum source and in combination define a vacuumed air evacuation area that functions as a workstation between the plate members. Thus, a user can easily position an object of choice within the workstation, or even adjacent thereto, and have hands free controlled access that allows manipulation of the object yet protects the user, and others, from physical or airborne transference of bacterial matter and from any undesirable odors emitting there from and also protects the user's eyes from any potential damage, respectively. Furthermore, the workstation is portable, self-contained, safe, sanitary and is substantially usable with any object of choice.

14 Claims, 1 Drawing Sheet

MULTIPURPOSE, SELF-CONTAINED, PORTABLE AND ODOR-FREE WORKSTATION

FIELD OF THE INVENTION

This invention relates in general to new and improved types of hands-on workstations that allow a user complete hands-free access to an object that is to be manipulated or worked on when positioned within and/or adjacent the workstation. However, the present invention more particularly pertains to a workstation that includes two transparent spaced apart plate members that define the workstation there between and the user can visually see the object there through. Furthermore, the workstation provides a vacuum source for air evacuation from the workstation so as to eliminate any foul odors associated with the object and in turn provide a safe, comfortable, odor-free workstation for the user.

BACKGROUND OF THE INVENTION

Within the known prior art, there have been numerous attempts to provide different types of workstations that may be used for hands-on work and the like. However, most types of workstations are designed for a specific type of job at hand and are therefore limited to a specific use. Unfortunately, heretofore there has not been a successful multipurpose, self-contained, portable and odor-free workstation that allows for a user to work on any type of object of choice, and/or perform any job at hand in a safe convenient manner as taught herein. Also, the uses for the present invention are to numerous to mention, such as this invention may be used for not only for removal of odors associated with object or worksite, but also eliminates any other unwanted contaminants from the surrounding ambient air, such as gaseous materials including but not limited too, aerosol, chemical odors, vapors, smoke, particulate matter, etc. In fact, in order to provide an improved comfortable workstation the invention further includes an optional pleasant scent system if so desired which is most advantageous.

Some examples of prior art workstations are disclosed within U.S. Pat. No. 6,663,610, No. 4,921,492 and No. 5,015,243. Each of these references are somewhat relevant to the present invention as they each include a vacuum source used for evacuation of air from the work site while the object is being worked on. However, these references are clearly limited to use only for a specific job at hand, namely performing a surgical procedure.

Other types of workstations have been taught but none include the novel advantages and diversified uses as taught by the present invention as will be seen after reviewing the following specification.

SUMMARY OF THE INVENTION

It is therefore a primary object of the present invention to provide a workstation that may be used for substantially any type of work of user choice. For example, this workstation allows the user to position the object therein and perform any type of work upon the object that is needed, including soldering, gluing, burning, washing, welding, etc. and is thus a multi-purpose workstation and not limited to any particular type of work.

It is another object of the present invention to provide a workstation that is completely self-contained including a rechargeable battery. Whereby, the need for electrical power and/or a water supply or the like are eliminated.

Another object of the present invention is to provide a workstation that is completely portable as it is mounted on wheels, however for safety purposes the wheels should be of the locking caster type. Also, the workstation is completely adjustable for individual use as the user can adjust the workstation into any angular position and height to their personal liking and needs.

Still another object of the present invention is to provide a workstation that is safe and in the preferred embodiment includes suitable filter means of engineering choice. For example, the workstation may include a typical HEPA™ filter and/or ionized type filter and/or scent system. This is very important when working on an object that releases contaminants, gases, plumes, and/or foul odors or the like.

A primary object and purpose for the filter system of the workstation is to prevent airborne or physical transference of bacterial contamination from contaminants such as from fecal matter or the like, that could possibly result in diseases including but not limited too: Hepatitis, Streptococcal, Staphylococcal infections, *E coli* infections, etc.

Yet another object of the present invention is to provide a workstation that may include either brackets, shelves, hooks, and/or a storage compartment for support and containment of accessory items that may be associated with the job at hand. For example, the accessory items may be bottled liquids, chemicals, brushes, tools, storage bags, Kleenex™, Handy-wipes™, etc.

As an additional option, it may be desirable to include a disposal receptacle that is removably attached and in line with the noted air filter system at a location of choice. This would be most advantageous as this allows the user to conveniently dispose of unsanitary items associated with the job at hand, such as swabs, pouches, cotton-balls, pads, bandages, etc. Thus, upon disposing of the item within the noted disposal receptacle, being the receptacle is in line with the filter system, any foul odors associated with the item are conveniently removed and filtered along with the air. Therefore, providing a discrete odor-free means for containment of the item within the receptacle until the user wishes to empty the container upon their convenience without worry of embarrassing odors, etc.

Yet a further object of the present invention is to provide a workstation that is not only useful and odor free for the user, but also provides a pleasant odor-free atmosphere for the users assistant, and/or other persons such as a surgical team, whom otherwise would be subjected to foul odors associated with the job at hand. As a result, reducing embarrassment for the user as well as reducing stress and frustration for all involved.

Still another object of the present invention is to provide a workstation wherein the actual work platform namely the two transparent plate members that are interconnected to form one unit, is completely removable and dishwasher safe.

Another object of the present invention is to provide a workstation that includes a handle on the vacuum housing for ease of mobility.

Also another object of the present invention is to provide a workstation wherein the vacuum motor is of the more quiet type so as to be less disturbing and/or distracting for the user.

A further object of the present invention is to provide a workstation that is lightweight in construction, easily maneuverable and cost effective to manufacture and sell.

Other objects and advantages will be seen when taken into consideration with the following specification and drawing.

DETAILED DESCRIPTION OF THE DRAWING

Figure 1:
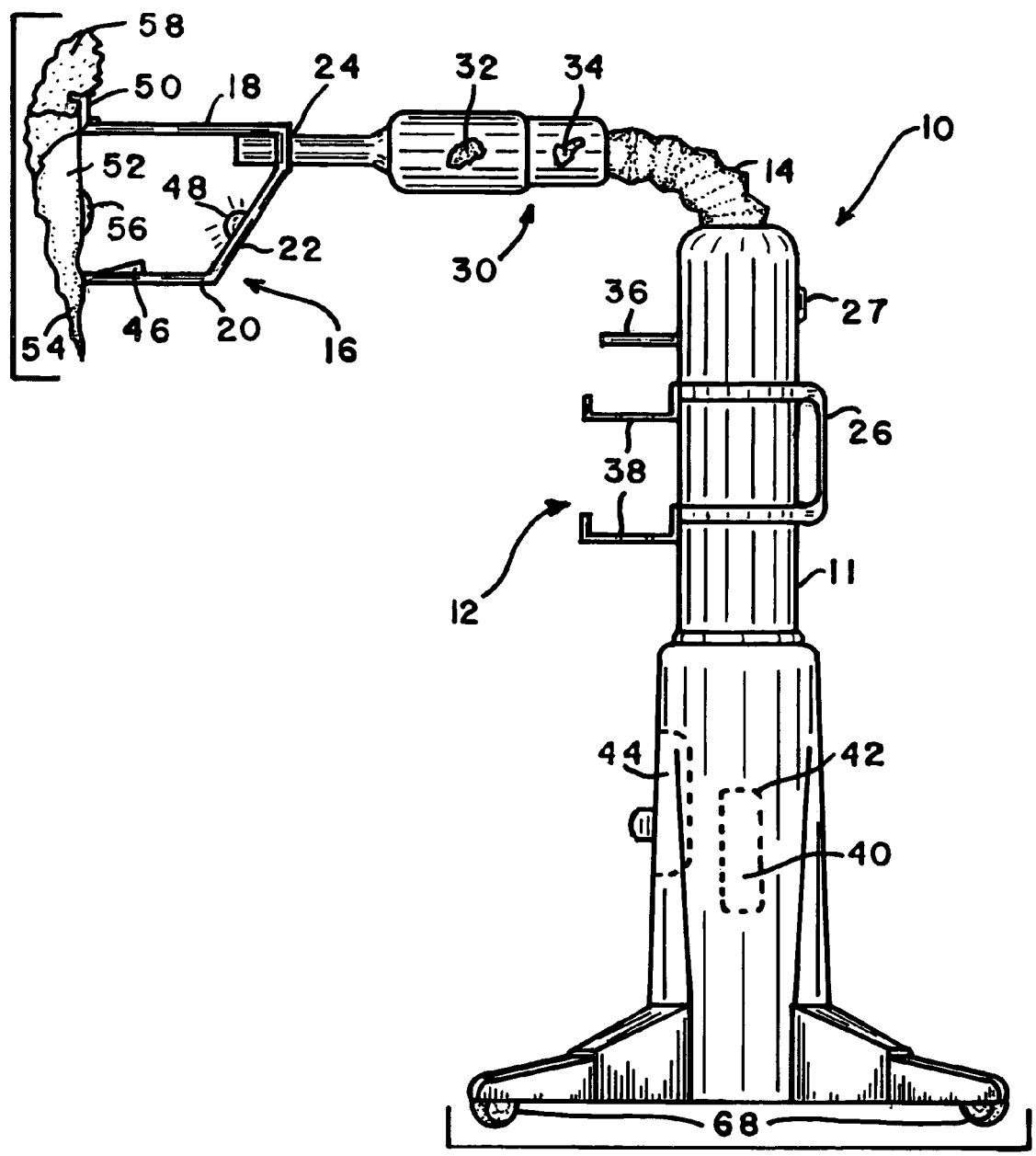
FIG. 1 is substantially an overview of the preferred embodiment for the present invention.

Referring now in detail to the drawing wherein like characters refer to like elements throughout the drawing. The present invention is substantially a multi-purpose workstation and is not to be limited to any specified type of work or particular job. However, for clarity and explanation for use and function the applicant has herein presented the workstation as being used by a patient who had a Colostomy operation and is using the workstation to attend to procedures associated therewith. Thus, it is to be understood although the following description defines a particular job at hand it is not to be limited thereto, and is therefore only exemplary of one possible use.

The present invention is a multipurpose, self-contained, portable, odor-free workstation represented by overview (10) including a vacuum source represented by overview (12) for providing air evacuation from the workstation (10). It is to be noted any suitable type of vacuum source of engineering choice may be incorporated, thus the particular workings and components associated with the vacuum are not taught herein as they are very well known in the art. However, it is desirable that the vacuum source (12) be contained within a suitable housing (11) that is lightweight, includes a handle (26) for ease of mobility and maneuvering the housing between various locations or positions of choice and which further is mounted on rollers (68) that in the preferred embodiment are of the locking caster type. It is to be further noted the housing (11) is adjustable between various heights of user choice by any suitable adjustment means. For example the housing (11) may be formed from two interconnecting members having a telescopic relationship such as depicted herein. Also, vacuum hose (14) further includes a replaceable air filter system (30) therein that is in line and in open communication with a filtered air outlet (27) located on housing (11) for expelling the filtered air there from.

The means for air evacuation from the workstation (10) is accomplished via a vacuum hose (14) that in the preferred embodiment is of the accordion style respectively, so as to be adjustable in length and easily manually manipulated into various positions of user choice. Vacuum hose (14) includes a first end that is operatively interconnected onto the vacuum source (12) and a second end that is operatively interconnected onto the work platform represented by overview (16). The work platform (16) is substantially formed from a first outwardly extending transparent plate member (18) and a second outwardly extending transparent plate member (20) in combination. Thus it can be seen in FIG. 1 that each transparent plate member (18 & 20) when attached in place are spaced apart and opposed to each other. Therefore having a spaced apart relationship that defines both an air evacuation area and the workstation there between.

In the preferred embodiment each transparent plate member (18 & 20) are interconnected via a downwardly facing extension member (22) that is integrally formed with each transparent plate member (18 & 20). Extension member (22) further includes attachment means for attaching the work platform (16) onto the second end of vacuum hose (14). As depicted herein the attachment means is in the form of a ring (24) respectively and is of a shape and size to be slidably adjustably engaged onto the second end of vacuum hose (14). As a result the position of the ring member (24) when secured onto the second end of hose member (14) provides the adjustment means for allowing the workstation to be variably positioned according to the user needs. It is to be noted this type of configuration and/or embodiment for the work platform (16) is most advantageous as the entire unit may be easily removed and placed in a dishwasher for cleansing if needed. However, it is to be understood that this embodiment is only exemplary of one possible style of attachment means and configuration, as numerous attachment means and/or various configurations for the plate members (18 & 20) are to be determined by engineering and/or end user preferences, therefore the invention is not to be limited to the embodiment as depicted herein.

In the preferred embodiment, the vacuum hose (14) also includes a replaceable air filter system represented by overview (30) therein between the first and second end thereof respectively. Any suitable type of air filter system may be used however it has been determined that a pre-existing Hepa™ filter system is most efficient and cost effective. Such a filter system includes an internal replaceable filter (32) that is housed within the main filter system (30) and also provides a replaceable scent system (34) for conditioning the filtered air and also providing a pleasant scented atmosphere that is very important.

With further reference to housing (11), it is to be noted the housing may also include at least one support means for support of workstation accessories thereon pertaining to the job at hand. The support means may be of any suitable type such as in the form of a hook, a bracket, a shelf, a removable pocket, or the like and the accessories are to be determined by end user preferences, for example, in this scenario the user may desire a support shelf (36) for support of a bottled substance thereon, (not shown). The user may further require brackets (38) for support of a Kleenex™ box, Zip-lock™ storage bags, pouches, lotions, Handy-Wipes™, towels, etc. or any other suitable accessory of choice.

Still further pertaining to housing (11), as previously noted the vacuum system (12) is self-contained and in the preferred embodiment is battery powered by a rechargeable battery source (40) contained within a easy access battery compartment (42) with both the battery source (40) and battery compartment (42) being depicted by ghost lines. Yet another advantage would be to include at least one storage compartment (44) for storage of any needed accessories with the storage compartment being depicted herein in ghost lines.

Further novel features for the present embodiment may include a mirror that functions as a visual aid for the user. For example as depicted herein, second outwardly extending transparent plate (20) has an adhesively attached preferably angled mirror (46) that is manually positioned and attached at a location of user choice. Yet another novel feature is to include a removable adhesively attached light source (48) that may be affixed at any location of user choice, such as any area upon the work platform (16) or upon the extension member (22) as depicted herein.

As previously noted, in use the present scenario is adapted for use by a colostomy patient attending to a stoma normally associated therewith. With this in mind another novel feature is to include upon the first outwardly extending transparent plate member (18) a pivotably attached hook member that functions as a shirt holder (50). This allows a user (52) to uplift and secure their shirt (58) upon shirt holder (50) and then position their body (54) against each exterior exposed edge of each outwardly extending transparent plate member (18 & 20) which in turn positions the object (56) within the evacuation workstation area. It may be further advantageous to partially shape each exterior exposed edge so as to conform to the shape of the user, respectively. Once in position the user has a complete hands-free access to the object and they can now attend to the job at hand in a safe, odor-free, pleasantly scented environment.

It can now be seen that the above description is most functional for the patient as noted. However, it is to be clearly understood that this invention is functional for numerous jobs at hand and is thus not limited to the present scenario.

Although the invention has been herein shown and described in what is conceived to be the most practical and preferred embodiment, it is recognized that departures may be made there from within the scope and spirit of the invention, which is not to be limited to the details disclosed herein but is to be accorded the full scope of the claims so as to embrace any and all equivalent devices and apparatuses.

The invention claimed is:

1. A multipurpose, self-contained, portable, odor-free, workstation comprising: a work platform and a vacuum source for providing air evacuation from the workstation via a vacuum hose, said vacuum hose having a first end and a second end, said first end is operatively interconnected to said vacuum source said work platform being integrally formed from a first outwardly extending transparent plate member and a second outwardly extending transparent plate member in combination that are integrally interconnected via a downwardly facing extension member, each said transparent plate member are spaced apart and opposed to each other thus having a spaced apart relationship which defines an air evacuation area in between each said transparent plate member, and said downwardly facing extension member having adjustable attachment means for attaching said work platform onto said second end of said vacuum hose, whereby;
a user can easily position an object of choice within said air evacuation area and have hands free controlled access therein that allows manipulation of said object yet protects said user from any undesirable odors emitting there from.

2. The multipurpose, self-contained, portable, odor-free, workstation of claim 1 wherein said vacuum hose further includes a replaceable air filter system therein.

3. The multipurpose, self-contained, portable, odor-free, workstation of claim 1 wherein said vacuum hose is further adjustable in length and easily manually manipulated into a position of choice.

4. The multipurpose, self-contained, portable, odor-free, workstation of claim 1 wherein said second end that is operatively interconnected onto said work platform is further removably and adjustably attached.

5. The multipurpose, self-contained, portable, odor-free, workstation of claim 1 wherein said vacuum source is further contained within a housing, and said housing being adjustable in height.

6. The multipurpose, self-contained, portable, odor-free, workstation of claim 5 wherein said housing further includes a handle thereon for maneuvering said housing between various locations or positions of choice.

7. The multipurpose, self-contained, portable, odor-free, workstation of claim 5 wherein said housing further includes at least one support means for support of workstation accessories thereon.

8. The multipurpose, self-contained, portable, odor-free, workstation of claim 1 wherein said vacuum source is battery powered.

9. The multipurpose, self-contained, portable, odor-free, workstation of claim 5 wherein said housing further includes at least one storage compartment.

10. The multipurpose, self-contained, portable, odor-free, workstation of claim 5 wherein said housing is mounted on rollers.

11. The multipurpose, self-contained, portable, odor-free, workstation of claim 10 wherein said rollers are lockable.

12. The multipurpose, self-contained, portable, odor-free, workstation of claim 2 wherein said replaceable air filter system further includes a pleasant scent.

13. The multipurpose, self-contained, portable, odor-free, workstation of claim 1 wherein said second outwardly extending transparent plate further includes a mirror thereon.

14. The multipurpose, self-contained, portable, odor-free, workstation of claim 1 wherein said work platform further includes a light source.

* * * * *